United States Patent [19]

Filbey

[11] 4,406,665

[45] Sep. 27, 1983

[54] DIESEL FUEL COMPOSITION

[75] Inventor: Allen H. Filbey, Bloomfield Hills, Mich.

[73] Assignee: Ethyl Corporation, Richmond, Va.

[21] Appl. No.: 408,074

[22] Filed: Aug. 16, 1982

[51] Int. Cl.$^3$ ............................................. C10L 1/22
[52] U.S. Cl. ................................ 44/53; 44/56; 44/57; 44/63; 549/475
[58] Field of Search .................... 44/53, 56, 57, 63; 549/475

[56] References Cited

U.S. PATENT DOCUMENTS

| | | | |
|---|---|---|---|
| 2,321,311 | 6/1943 | Mottlau et al. | 44/63 |
| 2,387,323 | 10/1945 | Gaynor et al. | 44/57 |
| 2,599,338 | 6/1952 | Lifson et al. | 44/63 |
| 2,858,200 | 10/1958 | Broughten | 44/57 |
| 3,311,559 | 3/1967 | Mottus | 44/63 |
| 3,380,815 | 4/1968 | Herbst | 44/57 |
| 4,191,536 | 3/1980 | Niebylski | 44/63 |

Primary Examiner—Charles F. Warren
Assistant Examiner—Y. Harris-Smith
Attorney, Agent, or Firm—Donald L. Johnson; John F. Sieberth; Joseph D. Odenweller

[57] ABSTRACT

Cetane number of diesel fuel, both hydrocarbon and alcohol, is increased by adding a small amount of a tetrahydrofuranol nitrate.

4 Claims, No Drawings

DIESEL FUEL COMPOSITION

BACKGROUND

Diesel engines operate by compression ignition. They have compression ratios in the range of 14:1 to 17:1 or higher and for that reason obtain more useful work from a given amount of fuel compared to an Otto cycle engine. Historically, diesel engines have been operated on a petroleum-derived liquid hydrocarbon fuel boiling in the range of about 300°–750° F. Recently, because of dwindling petroleum reserves, alcohol and alcohol-hydrocarbon blends have been studied for use as diesel fuel.

One major factor in disel fuel quality is cetane number. Cetane number is related to ignition delay after the fuel is injected into the combustion chamber. If ignition delays too long, the amount of fuel in the chamber increases and upon igniton results in a rough running engine and increased smoke. A shot ignition delay results in smooth engine operation and decreases smoke. Commercial petroleum diesel fuels generally have a cetane number of about 40–55. Alcohols have a much lower cetane value and require the addition of a cetane improver for successful engine operation.

Through the years, many types of additives have been used to raise the cetane number of diesel fuel. These include peroxides, nitrites, nitrates, nitrosocarbamates, and the like. Alkyl nitrates such as amyl nitrate, hexyl nitrate and mixed octyl nitrates have been used commercially with good results.

SUMMARY

According to the present invention a cyclic ether nitrate is provided which gives a substantially higher cetane number increase than that obtained by adding the same amount of an alkyl nitrate such as isooctyl nitrate.

DESCRIPTION OF THE PREFERRED EMBODIMENTS

A preferred embodiment of the invention is a liquid fuel adapted for use in a diesel engine, said fuel being selected from the group consisting of liquid hydrocarbons of the diesel boiling range, alcohols and mixtures thereof, said fuel containing a cetane number increasing amount of a tetrahydrofuranol nitrate.

Illustrative examples of tetrahydrofuranol nitrates include 3-(4-methyltetrahydrofuranol)nitrate, 3-(5-methyltetraydrofuranol)nitrate, 3-(5-isobutyltetrahydrofuranol)nitrate, 3-(4,5-dimethyltetrahydrofuranol)nitrate, 3-(4-sec-dodecyltetrahydrofuranol)nitrate, 3-(4-sec-eicosyltetrahydrofuranol)nitrate, 3-(4-chlorotetrahydrofuranol)nitrate, 3-(5-bromotetrahydrofuranol)nitrate, 3-(4-ethyl-5-chlorotetrahydrofuranol)nitrate, 2-tetrahydrofuranol nitrate, and the like. Caution: tetrahydrofuranol nitrate is explosive.

A more preferred class of tetrahydrofuranol nitrates include those having the structure

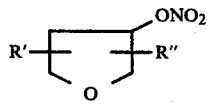

wherein R' and R" are independently selected from the group consisting of hydrogen, alkyl containing 1-20 carbon atoms, cycloalkyl containing 5-8 carbon atoms, alkenyl containing 2-20 carbon atoms, aryl containing 6-12 carbon atoms and aralkyl containing 7-12 carbon atoms.

Representative examples of this preferred class include 3-tetrahydrofuranol nitrate, 3-(5-methyltetrahydrofuranol)nitrate, 3-(4-n-butyltetrahydrofuranol)nitrate, 3-(5-sec-dodecyltetrahydrofuranol)nitrate, 3-(2,5-dimethyltetrahydrofuranol)nitrate, 3-(5-n-octadecyltetrahydrofuranol)nitrate, 3-(5-sec-eicosyltetrahydrofuranol)nitrate, 3-(5-cyclopentyltetrahydrofuranol)nitrate, 3-(4-cyclohexyltetrahydrofuranol)nitrate, 3-[4-(ethylcyclohexyl)tetraydrofuranol]nitrate, 3-(5-vinyltetrahydrofuranol)nitrate, 3-(5-dodecenyltetrahydrofuranol)nitrate, 3-(4-octadecenyltetrahydrofuranol)nitrate, 3-(5-eicosenyltetrahydrofuranol)nitrate, 3-(5-phenyltetrahydrofuranol)nitrate, 3-(4-phenyltetrahydrofuranol)nitrate, 3-(5-naphthyltetrahydrofuranol)nitrate, 3-[5-(4-methylphenyl)tetrahydrofuranol]nitrate, 3-(4-benzyltetrahydrofuranol)nitrate, 3-[4-($\alpha$-methylbenzyl)tetrahydrofuranol]nitrate, 3-[5-($\alpha$,$\alpha$-dimethylbenzyl)tetrahydrofuranol]nitrate, 3-[5-(p-tert-phenyl)-tetrahydrofuranol]nitrate, and the like.

The most preferred cetane improver is 3-tetrahydrofuranol nitrate.

The amount of cetane improver added depends on the type of fuel being used, the initial cetane value, and the amount of cetane number increase desired. Alcohol fuel such as methanol, ethanol, isopropanol, isobutanol, hexanol, and the like, have very low cetane values and large amounts of cetane improvers are required. A useful range in which to operate is about 5–25 weight percent cetane improver.

Blends of alcohol and petroleum derived diesel fuel have higher cetane values and require less cetane improver. A useful range is about 0.5–10 weight percent.

Petroleum derived distillate fuels in the diesel boiling range require only small amounts of cetane improver to achieve a significant increase in cetane number. Such fuels without any cetane improver generally have cetane numbers in the range of about 25–60. Cetane numbers in the range of 25–35 are considered low and those in the range of 50–60 are considered top grade diesel fuels. Diesel fuels in the 35–50 mid-range are most common. An object of the invention is to upgrade the low cetane number fuels at least into the mid-range and to increase the cetane value of the mid-range fuels into the upper portion of the mid-range (e.g. 45–50) or even into the premium range above 50. It has been found that highly beneficial results can be achieved using as little as 0.05 weight percent of the present additive which has been shown to give a cetane number boost of over 3. Using only 0.15 weight percent has resulted in a cetane number increase of almost 10. Accordingly, a useful concentration range in petroleum derived diesel fuel is about 0.01–5 weight percent and more preferably about 0.05–0.5 weight percent.

Prepration of 3-tetrahydrofuranol nitrate by the reaction of thallium (III) nitrate with 3-buten-1-ol in pentane solvent and by the reaction of 3-hydroxytetrahydrofuran with an acetic acid-nitric acid mixture has been reported (R. J. Ouellette et al, *J. Org. Chem.* 41, pages 2782-3).

The following example shows the preparation of 3-tetrahydrofuranol nitrate by reaction of 3-hydroxytetrahydrofuran with a nitric acid-sulfuric acid mixture.

EXAMPLE 1

In a reaction vessel was placed 20 ml concentrated nitric acid. The nitric acid was cooled to −16° C. and then 9.2 ml. concentrated sulfuric acid, 17.4 ml 30 percent oleum and 0.2 g. urea was added. The mixture was stirred at −14° C. and 22 g. of 3-hydroxyltetrahydrofuran was added over a 75 minute period at −8° to −14° C. The reaction mixture was then quenched with 100 ml. ice water and then extracted with methylene chloride. The methylene chloride solution was neutralized with sodium bicarbonate and dried over anhydrous sodium sulfate. The methylene chloride solvent was distilled out at 40° C. 40 mm Hg to yield 27.25 g. of 3-tetrahydrofuranol nitrate.

Other tetrahydrofuranol nitrates can be made following the above general procedure using substituted 3-hydroxytetrahydrofurans.

The cetane increases caused by the present additives was measured in comparison with that caused by a commercial cetane improver, isooctyl nitrate, using a standard cetane engine. The fuel used was a commercial No. 2 petroleum diesel fuel. The results at various concentrations of 3-tetrahydrofuranol nitrate and isooctyl nitrate are shown in the following table.

TABLE

| Concentration | Isooctyl Nitrate | | 3-Tetrahydrofuranol Nitrate | |
|---|---|---|---|---|
| | CN | Increase | CN | Increase |
| None | 45.83 | — | 45.83 | — |
| 0.05 | 48.01 | 2.2 | 49.26 | 3.4 |
| 0.10 | 51.13 | 5.3 | 51.50 | 5.6 |
| 0.15 | 52.33 | 6.5 | 54.28 | 8.4 |

These results show that the tetrahydrofuranol nitrate is not only more effective at very low concentration but surprisingly continues to give a cetane number increase that is almost linear with concentrations wherein the effectiveness of the alkyl nitrate is not linear above a concentration of 0.10 weight percent.

Other conventional additives may be included in the diesel fuel including antioxidants, pour point depressants, cold filter plugging inhibitors, detergents, rust inhibitors, and the like including other cetane improvers.

I claim:

1. Liquid fuel adapted for use in a diesel engine, said fuel being selected from the group consisting of liquid hydrocarbons of the diesel boiling range, alcohols and mixtures thereof, said fuel containing a cetane number increasing amount of a tetrahydrofuranol nitrate.

2. A fuel composition of claim 1 wherein said fuel is said liquid hydrocarbon of the diesel boiling range.

3. A fuel composition of claim 2 wherein said tetrahydrofuranol nitrate has the structure

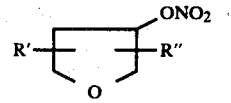

wherein R' and R" are independently selected from the group consisting of hydrogen, alkyl containing 1–20 carbon atoms, cycloalkyl containing 5–8 carbon atoms, alkenyl containing 2–20 carbon atoms, aryl containing 6–12 carbon atoms and aralkyl containing 7–12 carbon atoms.

4. A fuel composition of claim 3 wherein said tetrahydrofuranol nitrate is 3-tetrahydrofuranol nitrate.

* * * * *